United States Patent
Nevler et al.

(10) Patent No.: US 10,646,406 B2
(45) Date of Patent: *May 12, 2020

(54) NASOGASTRIC TUBE

(71) Applicant: ENVIZION MEDICAL LTD., Tel Aviv (IL)

(72) Inventors: Avinoam Nevler, Reut (IL); Orit Shaked, Ramat Yishai (IL); Eyal Haytman, Kfar Vradim (IL)

(73) Assignee: ENVIZION MEDICAL LTD., Tel Aviv (IL)

( * ) Notice: Subject to any disclaimer, the term of this patent is extended or adjusted under 35 U.S.C. 154(b) by 357 days.

This patent is subject to a terminal disclaimer.

(21) Appl. No.: 15/447,892

(22) Filed: Mar. 2, 2017

(65) Prior Publication Data

US 2017/0239148 A1 Aug. 24, 2017

Related U.S. Application Data

(63) Continuation of application No. 13/982,289, filed as application No. PCT/US2012/046850 on Jul. 16, 2012, now Pat. No. 9,839,584.

(60) Provisional application No. 61/508,670, filed on Jul. 17, 2011.

(51) Int. Cl.
*A61H 21/00* (2006.01)
*A61H 9/00* (2006.01)
*A61J 15/00* (2006.01)
*A61M 1/00* (2006.01)

(52) U.S. Cl.
CPC ........ *A61J 15/0003* (2013.01); *A61H 9/0057* (2013.01); *A61H 21/00* (2013.01); *A61J 15/003* (2013.01); *A61J 15/0073* (2013.01); *A61M 1/0035* (2014.02); *A61M 1/0037* (2013.01); *A61H 2201/105* (2013.01); *A61H 2201/5005* (2013.01)

(58) Field of Classification Search
CPC .... A61J 15/003; A61J 15/0003; A61M 39/22; A61M 39/223; A61M 2039/224; A61B 17/3478; A61B 2017/00269; A61B 2017/306; A61F 2/04; A61F 5/0069
See application file for complete search history.

(56) References Cited

U.S. PATENT DOCUMENTS

| | | |
|---|---|---|
| 4,356,824 A | 11/1982 | Vazquez |
| 4,904,238 A | 2/1990 | Williams |
| 4,968,307 A | 11/1990 | Dake et al. |

(Continued)

FOREIGN PATENT DOCUMENTS

| | | |
|---|---|---|
| EP | 2301512 | 9/2009 |
| EP | 2301512 | 3/2011 |

(Continued)

*Primary Examiner* — Bhisma Mehta
*Assistant Examiner* — William R Frehe
(74) *Attorney, Agent, or Firm* — The Roy Gross Law Firm, LLC; Roy Gross

(57) ABSTRACT

A nasogastric tube (10) including a main lumen (12) having one or more proximal connectors (14) for connecting to a source of substances or pressure, and one or more vacuum lumens (16) peripherally surrounding the main lumen (12), each vacuum lumen (16) including a vacuum sealing portion (24), which includes one or more suction ports (26) for sealingly drawing an inner wall of an esophagus thereagainst.

12 Claims, 2 Drawing Sheets

(56) References Cited

U.S. PATENT DOCUMENTS

| | | | |
|---|---|---|---|
| 5,389,074 A | 2/1995 | Parker et al. | |
| 5,707,351 A * | 1/1998 | Dorsey, III | A61M 1/0062 604/30 |
| 6,126,647 A | 10/2000 | Posey et al. | |
| 6,165,164 A | 12/2000 | Hill et al. | |
| 6,695,764 B2 * | 2/2004 | Silverman | A61F 2/04 600/29 |
| 6,790,214 B2 | 9/2004 | Kraemer et al. | |
| 6,949,092 B1 | 9/2005 | Moss | |
| 7,794,425 B2 | 9/2010 | Gobel | |
| 7,967,780 B2 | 6/2011 | Goebel | |
| 8,100,874 B1 | 1/2012 | Jordan et al. | |
| 8,453,648 B2 | 6/2013 | Black et al. | |
| 9,789,029 B2 | 10/2017 | Besser et al. | |
| 9,839,584 B2 * | 12/2017 | Nevler | A61J 15/003 |
| 2003/0208209 A1 | 11/2003 | Gambale et al. | |
| 2004/0082909 A1 | 4/2004 | Shia et al. | |
| 2004/0153098 A1 * | 8/2004 | Chin | A61B 17/00008 606/129 |
| 2004/0220515 A1 | 11/2004 | Constantz | |
| 2005/0059962 A1 * | 3/2005 | Phan | A61B 18/1492 606/41 |
| 2005/0137574 A1 | 6/2005 | Sakal et al. | |
| 2008/0077043 A1 | 3/2008 | Malbrain et al. | |
| 2008/0195047 A1 | 8/2008 | Price | |
| 2009/0069796 A1 | 3/2009 | Oskin | |
| 2009/0306626 A1 | 12/2009 | Sinha et al. | |
| 2009/0317760 A1 | 12/2009 | Gadbois | |
| 2010/0030133 A1 | 2/2010 | Elia et al. | |
| 2011/0046653 A1 * | 2/2011 | Addington | A61B 5/04882 606/196 |
| 2011/0130650 A1 | 6/2011 | Dayan et al. | |
| 2012/0150111 A1 | 6/2012 | Hershey et al. | |
| 2013/0158471 A1 | 6/2013 | Neel et al. | |
| 2013/0310806 A1 | 11/2013 | Nevler et al. | |
| 2014/0066880 A1 | 3/2014 | Prince et al. | |
| 2014/0088359 A1 | 3/2014 | Quaye | |
| 2014/0100531 A1 | 4/2014 | Ankrum et al. | |
| 2014/0188080 A1 | 7/2014 | Besser et al. | |
| 2014/0235960 A1 | 8/2014 | Addington et al. | |
| 2015/0174013 A1 | 6/2015 | Besser et al. | |

FOREIGN PATENT DOCUMENTS

| | | | |
|---|---|---|---|
| EP | 2301512 A2 * | 3/2011 | A61J 15/003 |
| WO | 2003034976 | 5/2003 | |
| WO | 2007095541 | 8/2007 | |
| WO | 2013012774 | 1/2013 | |
| WO | 2015198297 | 11/2015 | |
| WO | 2016024260 | 2/2016 | |

* cited by examiner

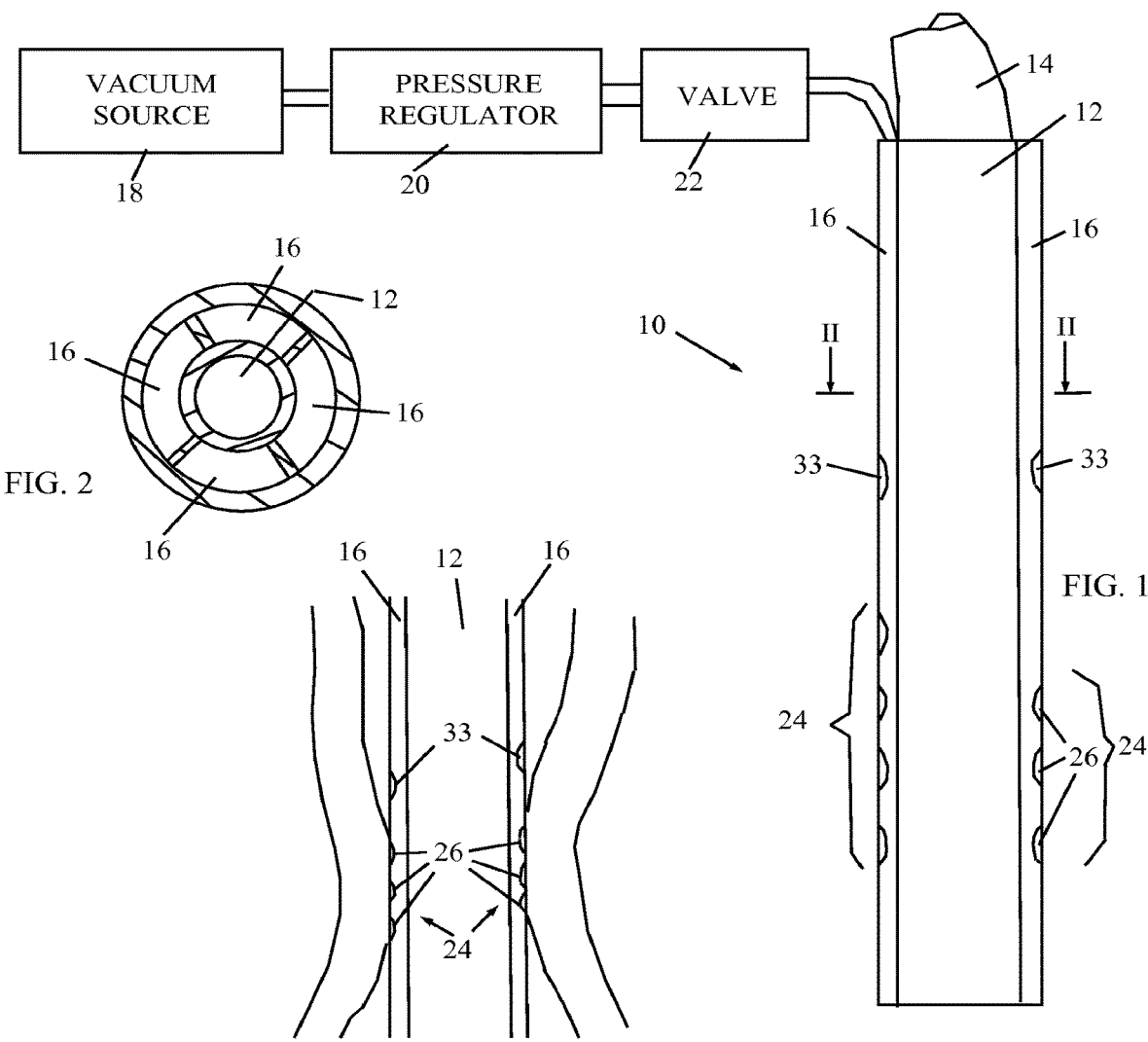

NASOGASTRIC TUBE

This application is a continuation of U.S. Ser. No. 13/982,289 filed Jul. 29, 2013, which is a national stage entry of PCT/US12/46850 filed on Jul. 16, 2012, which claims priority to U.S. Ser. No. 61/508,670 filed on Jul. 17, 2011. These applications are incorporated herein by reference as if fully set forth.

FIELD OF THE INVENTION

The present invention relates generally to nasogastric tubes.

BACKGROUND OF THE INVENTION

Enteral feeding is a form of hyperalimentation and metabolic support in which nutrient formulas or medicaments are delivered directly to the GI tract, either to the stomach or the duodenum. A nasogastric tube (NGT) is used for feeding and administering drugs and other oral agents. The tube is inserted into the patient's esophagus and stomach in order to ensure the passage of the agents into the stomach and not into the lungs. The NGT can also be used for sucking fluids from the stomach.

However, the use of NGTs can have disadvantages. Minor complications include nose bleeds, sinusitis, and a sore throat. Sometimes more significant complications occur including erosion of the nose where the tube is anchored, esophageal perforation, pulmonary aspiration, a collapsed lung, or intracranial placement of the tube.

Even worse, during feeding, excessive gastric pressure may result. From time to time, the body relieves such excess gastric pressure by expelling gas or liquid or reflux fluid. The fluids are expelled from the stomach through the esophagus to the mouth or nasal pathways. The reflux fluids may be inhaled into the lungs with possible risk of aspiration pneumonia, bacterial infection in the pharynx or esophagus or any other ailments. Accordingly, numerous studies have linked the use of the NGT to an increase in ventilator-associated pneumonia (VAP). VAP is the most common nosocomial infection in the intensive care unit (ICU), and it is associated with prolonged hospitalization, increased health care costs, and high attributable mortality.

There thus exists a pressing need for an NGT that is capable of significantly reducing the risk of reflux food and developing VAP.

SUMMARY OF THE INVENTION

The present invention seeks to provide a novel nasogastric tube, as is described more in detail hereinbelow. The NGT includes a tube and a vacuum control unit. The vacuum control unit couples the esophagus to the tube thus disabling the reflux of the food along the esophagus to the trachea. The NGT can be used in ICU, or elsewhere, in order to reduce the complications associated with reflux such as the risk of VAP.

The present invention overcomes the problems associated with prior art NGTs by sealing between the NGT and the inner wall of the esophagus. In a preferred embodiment, the inner wall of the esophagus is drawn by negative pressure (vacuum) towards and against the outer contour of the NGT. A vacuum control unit, which is connected to the hospital vacuum unit or any other vacuum unit, enables either simultaneous vacuum pressure in one or more suction units of the NGT or changeable vacuum pressure between the different suction units. In this way, the NGT of the present invention prevents reflux and aspiration of substances or liquids into the patient's lungs, while obviating the need to remove and replace the entire device from the patient's esophagus.

In another embodiment, the NGT of the present invention may be used in other places in the GI tract.

There is provided in accordance with an embodiment of the present invention a nasogastric tube including a main lumen having one or more proximal connectors for connecting to a source of substances (such as for feeding food or introducing drugs or other substances) or pressure, and one or more vacuum lumens peripherally surrounding the main lumen, each vacuum lumen including a vacuum sealing portion, which includes one or more suction ports for sealingly drawing an inner wall of an esophagus thereagainst.

In accordance with an embodiment of the present invention a vacuum source is connected to the one or more vacuum lumens. Some of the vacuum lumens may have more suction ports than others of the vacuum lumens. The vacuum lumens may be connected to the vacuum source via a pressure regulator and a valve.

There is also provided in accordance with an embodiment of the present invention a method including introducing the nasogastric tube into an esophagus of a patient, and applying vacuum to the one or more suction ports so as to sealingly draw an inner wall of an esophagus thereagainst.

The method may further include regulating the vacuum so that a suction level is not constant over time in the vacuum sealing portions.

The method may further include suction of saliva or other oropharyngeal secretions via one or more suctions ports that are proximal to the vacuum sealing portion.

BRIEF DESCRIPTION OF THE DRAWINGS

The present invention will be understood and appreciated more fully from the following detailed description taken in conjunction with the drawings in which:

FIG. 1 is a simplified schematic illustration of a nasogastric tube, constructed and operative in accordance with a non-limiting embodiment of the present invention;

FIG. 2 is a simplified sectional illustration of the NGT of FIG. 1, taken along lines II-II in FIG. 1;

FIG. 3 is a simplified schematic illustration of the nasogastric tube being used to suck and seal the inner wall of the esophagus against the NGT, in accordance with an embodiment of the present invention.

DETAILED DESCRIPTION OF EMBODIMENTS

Figure 4:
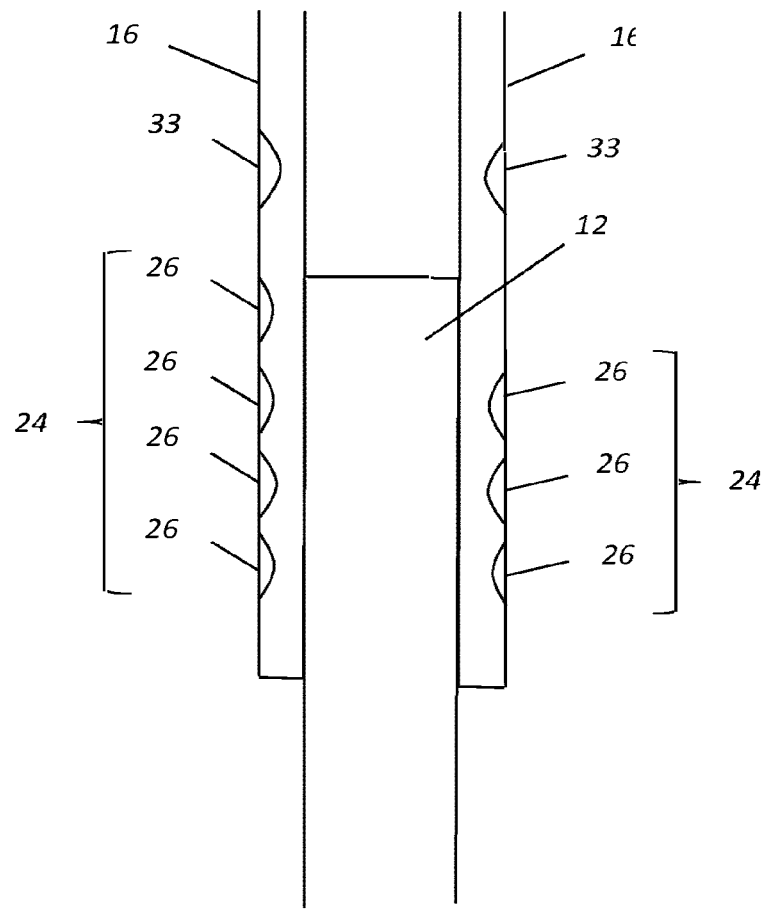
FIG. 4 is an illustration of the nasogastric tube of FIG. 1 having the vacuum lumens as a separate unit from the main lumen and which is slid over the main lumen.

Reference is now made to FIGS. 1 and 2, which illustrate a nasogastric tube 10, constructed and operative in accordance with a non-limiting embodiment of the present invention.

NGT 10 includes a main (typically, but not necessarily, central) lumen 12. Main lumen 12 may be used to feed and administer drugs and other oral agents, and may also be used for sucking fluids from the stomach. As such, as is known in the art, main lumen 12 may be a double lumen, one lumen for feeding and the other lumen for suction (not to be confused with the vacuum lumens mentioned later). Main lumen 12 is provided with one or more suitable proximal connectors 14 for connecting to a source of substances for feeding or administering, and optionally to a source of pressure (e.g., suction), as is known in the art.

NGT 10 includes one or more vacuum lumens 16 that peripherally surround main lumen 12. The term "peripherally surround" as used in the description and claims, encompasses continuous surrounding (no gaps between the vacuum lumens or one continuous, peripheral vacuum lumen) and discontinuous surrounding (wherein there are separations between discrete vacuum lumens), In one embodiment, illustrated in FIG. 2, there are four vacuum lumens 16 peripherally spaced around main lumen 12; the invention is not limited to this number of vacuum lumens. The vacuum lumens 16 may be equally or unequally spaced from each other. Main lumen 12 and vacuum lumens 16 are thus arranged as concentrically arranged conduits. Vacuum lumens 16 are connected to a vacuum source 18, such as via a pressure regulator 20 and a valve 22, which form a vacuum control unit.

Main lumen 12 may be constructed from any suitable biocompatible material, such as but not limited to, polyurethane, silicone, polyvinyl chloride and many others. The vacuum lumens 16 may be constructed of similar materials, but alternatively may be constructed of medically safe metals, such as but not limited to, stainless steel, titanium alloys, NITINOL and others. Generally, without limitation, main lumen 12 may have a length in the range of 50 to 130 cm, with an outside diameter in the range of 5-12 Fr.

The main lumen 12 and the vacuum lumens 16 may be constructed as one unit. Alternatively, vacuum lumens 16 may be a separate unit which is slid over main lumen 12, as illustrated at FIG. 4, after insertion of main lumen 12 into the patient. As another alternative, vacuum lumens 16 may be first introduced into the patient, and main lumen 12 may be slid through the vacuum lumens 16.

Each vacuum lumen 16 includes a vacuum sealing portion 24, which includes one or more suction ports 26. As seen in FIG. 1, some vacuum lumens 16 may have more suction ports than others. As seen in FIG. 3, upon application of vacuum from vacuum source 18, the inner wall of the esophagus is drawn by negative pressure towards and against suction ports 26 (the outer contour of NGT 10). The outer contour of NGT 10, at least at vacuum sealing portion 24, is preferably round (circular or oval), for better conforming to and sealing the esophagus. In one embodiment, the vacuum sealing restricts at least 60% of the passage through the esophagus.

Pressure regulator 20 may be used to reduce or otherwise regulate the negative pressure from vacuum source 18. For example, pressure regulator 20 may be used to match the vacuum level from vacuum source 18 to the vacuum level needed in vacuum sealing portion 24. The valve 22 may be used to shift the vacuum between the different vacuum lumens 16 so that the suction level is not constant over time in the vacuum sealing portion 24, which may provide variability in how the esophagus wall is sucked in, and for how long.

NGT 10 may be provided with different numbers of vacuum sealing portions 24 and suction ports 26, and the vacuum to the sealing portions 24 may be regulated so as to create peristaltic movement or other oscillatory movement of the esophagus.

In accordance with an embodiment of the invention, one or more auxiliary suction ports 33 are provided proximal to vacuum sealing portion 24. Since vacuum sealing portion 24 seals off the esophagus, any oropharyngeal secretions, such as saliva, may accumulate above (i.e., proximal to) vacuum sealing portion 24. Auxiliary suction ports 33 may be used to suck and remove such secretions.

Vacuum source 18 is preferably activated following the insertion and localization of NGT 10 in the esophagus in order to reduce the risk of VAP, or other bacterial infections, by preventing or minimizing reflux food and liquid aspiration into the lungs.

One method of using NGT 10 of the present invention includes the following steps, without limitation and not necessarily in sequential order:

a) introducing NGT 10 into the esophagus of the subject;
 b) applying vacuum to the vacuum sealing portion(s) 24;
 c) adjusting the vacuum level (which may be done before step a); and
 d) after achieving a desired sealing of the esophagus wall to NGT 10, changing the vacuum intervals between the vacuum lumens 16, manually or automatically, such that NGT 10 remains intact to the esophagus.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

The invention claimed is:

1. A method for supplying substances or pressure to a stomach and/or duodenum of a patient, while sealing an esophagus against reflux, the method comprising:
  introducing a tube through the esophagus of the patient, said tube comprising:
   a main lumen having one or more proximal connectors connectable to a source of substances or pressure and a distal end configured to be positioned within the stomach and/or duodenum when in use, the distal end comprising an opening that during use allows access to the stomach and/or duodenum for the substances or pressure; and
   at least four vacuum lumens peripherally surrounding said main lumen, each of said vacuum lumens comprising a vacuum sealing portion; wherein a distance between said opening in the distal end and said vacuum sealing portions is such that when said distal end is positioned within the stomach and/or duodenum, each of said vacuum sealing portions is located within the esophagus, wherein each of said vacuum sealing portions comprises one or more suction ports; and
  applying vacuum to said one or more suction ports so as to circumferentially and sealingly draw an inner wall of the esophagus against the one or more suction ports, thereby disabling reflux.

2. The method according to claim 1, further comprising regulating a vacuum so that a suction level is not constant over time in said vacuum sealing portions.

3. The method of according to claim 1, wherein said at least four vacuum lumens comprise more than one vacuum sealing portion.

4. The method of claim 3, further comprising regulating a vacuum to said more than one vacuum sealing portion of said at least four vacuum lumens.

5. The method of claim 4, wherein regulating the vacuum to said more than one vacuum sealing portion comprises regulating the vacuum so as to create peristaltic movement or other oscillatory movement of the esophagus.

6. The method according to claim 1, further comprising supplying the substances or pressure to the stomach and/or duodenum of the patient through the opening in the distal end of said tube, while the esophagus is sealed against each of said vacuum sealing portions.

7. The system according to claim 1, wherein each of said vacuum sealing portions comprises at least two suction ports.

8. The system according to claim 1, wherein the tube is made from a biocompatible material.

9. The system according to claim 1, wherein the tube is made from polyurethane, silicone, polyvinyl chloride stainless steel, titanium alloys, nickel titanium, or any combination thereof.

10. The system according to claim 1, wherein the main lumen has a length of 50 to 130 cm.

11. The system according to claim 1, wherein the main lumen has an outer diameter in the range of 5-12 Fr.

12. The system according to claim 1, wherein each said vacuum sealing portion of said at least four vacuum lumens are round or oval.

* * * * *